(12) United States Patent
Bakay et al.

(10) Patent No.: US 12,364,509 B2
(45) Date of Patent: Jul. 22, 2025

(54) UTERUS MANIPULATOR IN MINIMALLY INVASIVE SURGERY

(71) Applicant: ONDOKUZ MAYIS UNIVERSITESI, Atakum/Samsun (TR)

(72) Inventors: Abdulkadir Bakay, Atakum/Samsun (TR); Onur Yontar, Atakum/Samsun (TR)

(73) Assignee: ONDOKUZ MAYIS UNIVERSITESI, Atakum/Samsun (TR)

( * ) Notice: Subject to any disclaimer, the term of this patent is extended or adjusted under 35 U.S.C. 154(b) by 328 days.

(21) Appl. No.: 18/042,504

(22) PCT Filed: Sep. 7, 2021

(86) PCT No.: PCT/TR2021/050898
§ 371 (c)(1),
(2) Date: Feb. 22, 2023

(87) PCT Pub. No.: WO2022/055457
PCT Pub. Date: Mar. 17, 2022

(65) Prior Publication Data
US 2023/0320752 A1     Oct. 12, 2023

(30) Foreign Application Priority Data
Sep. 9, 2020   (TR) .................................. 2020/14297

(51) Int. Cl.
*A61B 17/42* (2006.01)
*A61B 17/04* (2006.01)
*A61B 17/3209* (2006.01)

(52) U.S. Cl.
CPC .......... *A61B 17/42* (2013.01); *A61B 17/0469* (2013.01); *A61B 17/3209* (2013.01); *A61B 17/4241* (2013.01); *A61B 2017/4225* (2013.01)

(58) Field of Classification Search
CPC .... A61B 2017/1121; A61B 2017/1139; A61B 2017/4216; A61B 2017/4225;
(Continued)

(56) References Cited

U.S. PATENT DOCUMENTS

2013/0289585 A1* 10/2013 Jones ................. A61B 17/4241
606/151
2014/0180282 A1* 6/2014 Brecheen ............... A61B 17/42
606/45

(Continued)

FOREIGN PATENT DOCUMENTS

| JP | 2015516226 A | 6/2015 |
|---|---|---|
| KR | 20100122237 A | 11/2010 |
| WO | 2017189442 A1 | 11/2017 |

OTHER PUBLICATIONS

PCT International Search Report and Written Opinion dated Dec. 13, 2021 for PCT International Application No. PCT/TR2021/050898, filed Sep. 7, 2021.

*Primary Examiner* — Martin T Ton
(74) *Attorney, Agent, or Firm* — Crose Law LLC; Bradley D. Crose

(57) ABSTRACT

The present invention relates to a uterus manipulator in minimally invasive surgery that facilitates procedures of manipulation of the uterus, incising and suturing of all kinds of tissue connected to the uterus and particularly, incising the cervico-vaginal tissue in a circular line in laparoscopic hysterectomy, that prevents the incidence of various complications during said procedures, and that can be actuated (driven) manually without requiring any external energy source.

4 Claims, 8 Drawing Sheets

(58) Field of Classification Search
CPC . A61B 17/0469; A61B 17/11; A61B 17/3209; A61B 17/42; A61B 17/4241
See application file for complete search history.

(56) References Cited

U.S. PATENT DOCUMENTS

2018/0235602 A1\* 8/2018 Dang ................ A61B 17/0625
2018/0325552 A1\* 11/2018 Weihe ............... A61B 18/1482

\* cited by examiner

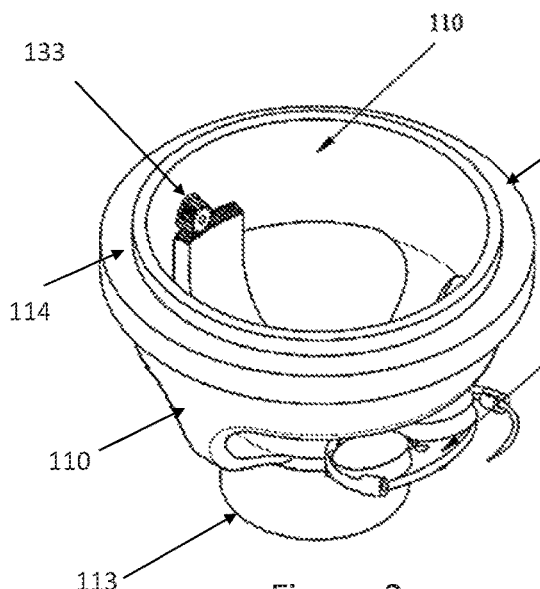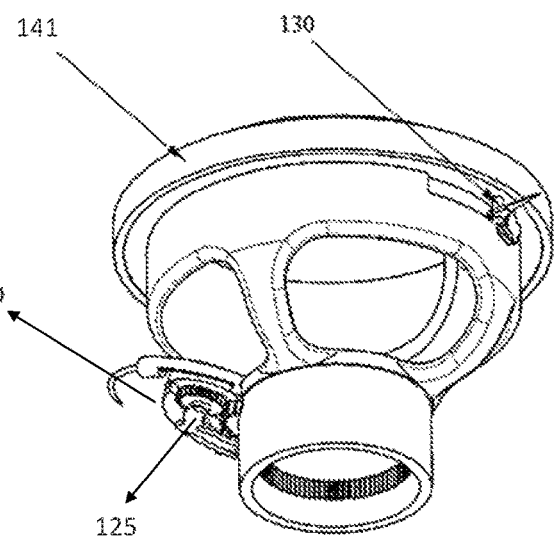
Figure 2
Figure 3

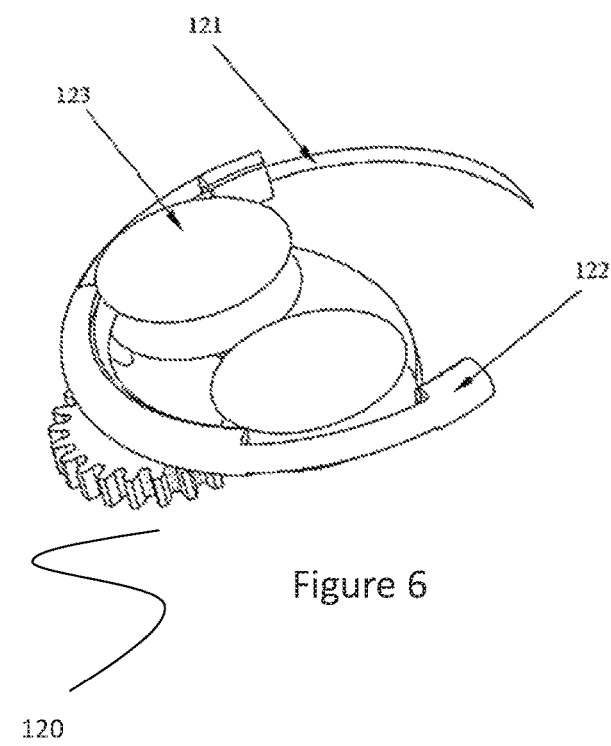
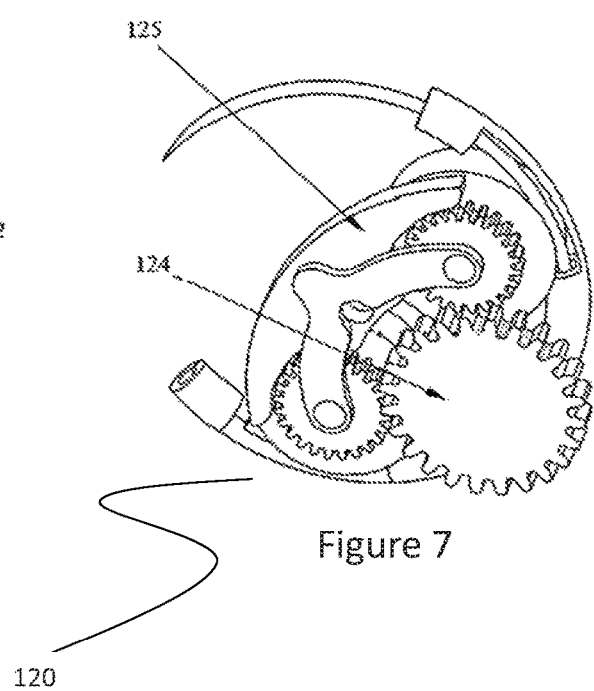
Figure 6
Figure 7

UTERUS MANIPULATOR IN MINIMALLY INVASIVE SURGERY

TECHNICAL FIELD OF THE INVENTION

The present invention relates to uterus manipulators that facilitate the procedure of incising and suturing of the uterus (womb) and related ligaments connected without harming other tissues, and that prevent the incidence of various complications during said procedures in laparoscopic hysterectomy.

Particularly, the present invention relates to a uterus manipulator used in minimally invasive surgery that can be actuated (driven) manually without requiring any external energy source during the procedures of manipulation of the uterus, incising and suturing of all kinds of tissue connected to the uterus and particularly, incising the cervico-vaginal tissue in a circular line in laparoscopic hysterectomy.

STATE OF THE ART

While surgery, by definition invasive surgery, is a procedure in which deliberate access to the body is gained via an incision, or percutaneous function, where instrumentation is used in addition to the puncture needle, in minimally invasive surgery, on the other hand, surgeons use tiny incisions in the skin, or no incisions at all, rather than the large cuts often needed in traditional surgery in order to cause less damage.

There are many procedures in which minimally invasive surgery is used. Some of these procedures are hysterectomy, adrenalectomy, nephrectomy, neurosurgery. A hysterectomy is a surgical procedure to remove the uterus (womb). In addition, it may also involve the removal of the cervix, ovaries (oophorectomy), fallopian tubes (salpingectomy), and other surrounding structures. It is an operation to remove the uterus surgically for various reasons, and it is the second most common surgery after cesarean section in women. Among the types of hysterectomy that can vary depending on the area removed, partial hysterectomy is the removal of the uterus without the cervix, while total or complete hysterectomy is the removal of the uterus and cervix, and radical hysterectomy is the removal of the uterus, cervix and, the upper part of vagina. Radical hysterectomy occasionally involves the removal of the fallopian tubes and ovaries. After any of these types of hysterectomy, the patient becomes infertile since the uterus, which is necessary for embryo implantation has been removed from the body.

First, vaginal hysterectomy (VAH) is encountered in case the types of hysterectomy, which also vary according to the application methods are examined. In a vaginal hysterectomy, the entire procedure is carried out through the vaginal canal and the uterus is removed by an incision made at the upper end of the passage. This offers significant advantages over the open surgical procedure described above, such as less associated complications, lower infection rate, shorter length of hospital stay, and shorter recovery time. Such surgeries are more frequently performed on women due to uterine prolapse. The vaginal removal of the uterus heals much faster than the incisions made in the abdomen, in this way, the patients can recover much more easily, return to their work more quickly, and the risks such as post-operative pain and infection are less observed. The uterine tissue is removed with an incision made from the vagina, and it is sutured such that there are no visible incisions in the abdomen. However, this method causes complications such as infection, internal bleeding, accumulation of blood under the sutures (hematoma) or in the abdomen, internal scar tissue blood clots (for example, thrombosis, deep venous thrombosis or pulmonary embolism).

Laparoscopic hysterectomy, also known as closed surgery, is an approach that involves making small incisions in the abdomen where laparoscopic instruments can be inserted in order to view the organs. This is also named keyhole surgery or minimally invasive surgery based on the abdominal procedure since it has a small incision size, low risk of operational injury, and faster post-operative recovery. Laparoscopic hysterectomy also enables the surgeons to perform more detailed examination and more complex operations than in vaginal hysterectomy, the procedure thereof begins with laparoscopic processes and ends with the removal of the uterus through the vaginal canal.

In hysterectomy, uterus manipulators have been developed for use in the surgery for removing the uterus and/or related organs. Said manipulators are surgical devices that are delivered to the patient's uterus through the vaginal route, that lend assistance to perform the main steps of the surgery and reduce the possibility of injuring other organs by enabling the uterus to move in the directions that the surgeon desires. According to its functions, it can also perform the processes of circular incising of the cervico-vaginal junction and suturing the opening created, which are the last steps of the surgery.

In the state of the art, the patent application numbered "TR 2016/12278" discloses a uterus manipulation device (uterus manipulator) that is used in the processes of manipulation of the uterus and facilitating the laparoscopic determination of the incision points of any tissue connected to the uterus, incising the cervico-vaginal junction tissue automatically by a manipulator, and suturing the opening created. The sheath of this manipulator provide assistance to disconnect the uterus manipulation device from the external environment, to carry the cable for the systems that require electricity, and also to carry the necessary transmission lines for performing any liquid or air application to the uterus. Additionally, after the incising procedure, the suturing procedure of the opening is performed by the surgeon. However, subsequent to incision of the cervico-vaginal junction in laparascopic hysterectomy surgery with the specified device, the opening that will be created before suturing may cause complications such as internal bleeding (internal bleeding), blood accumulation in the abdomen, internal scar tissue blood clots (for example, thrombosis, deep venous thrombosis, or pulmonary embolism). In addition to this, the device mentioned in the application numbered TR 2016/12278 requires electrical transmission and electrical source due to the systems thereof that require electrical energy, which makes the manipulation process dependent on another external source during hysterectomy. More importantly, the use of energy during colpotomy increases the possibility of the separating and rupturing, which is called a dehiscence complication in the literature, especially the opening of the sutured incision after the surgery.

In the state of the art, the patent application numbered "WO2020018046 A2" describes the uterus manipulators placed through vaginal route in the beginning of the surgery for the purpose of facilitating cutting of uterus (womb) an its related bonds without causing any damage to other tissues and laparoscopically suturing of the opening occurred afterwards in the hysterectomy (removal of the womb) procedure that is implemented laparoscopically. These manipulators have a structure that facilitates the manipulation of the uterus, cutting of all types of tissue connected to the uterus, cutting of the cervico-vaginal tissue by the device in a circular line using electrical energy, and suturing of the opening to be created intracorporeally (inside the abdomen) by means of the device. However, as it can be seen from the content of the patent application, the operations performed by the manipulator, incising and suturing of all types of tissue connected to the uterus are performed by using electrical energy, therefore, causing the manipulation process to be dependent on another energy modality and external source during hysterectomy. More importantly, the use of energy during colpotomy increases the possibility of the separating and rupturing, which is called a dehiscence complication in the literature, especially the opening of the sutured incision after the surgery.

Therefore, it is necessitated making an improvement in the relevant technical field since the available solutions for uterine manipulators increase the possibility of incidence of complications such as internal bleeding, accumulation of blood in the abdomen, internal scar tissue blood clots (e.g. thrombosis, deep venous thrombosis, or pulmonary embolism), and dehiscence during colpotomy, and are dependent on other energy modalities, external sources.

Objects of the Invention and Advantages Thereof

The present invention describes a uterus manipulator in minimally invasive surgery that can be actuated (driven) manually without requiring any external energy source during the manipulation of the uterus, suturing and incising of all kinds of tissue connected to the uterus, and particularly, suturing and incising of the cervico-vaginal tissue in a circular line in laparoscopic hysterectomy, that eliminates the disadvantages in the state of the art, and that prevents the incidence of complications such as internal bleeding, accumulation of blood in the abdomen, internal scar tissue blood clots (e.g. thrombosis, deep venous thrombosis, or pulmonary embolism), and dehiscence during colpotomy.

The most important object of the present invention is to obtain a uterus manipulator that can be actuated manually without requiring any external energy source during the procedures of suturing and incising of all kinds of tissue connected to the uterus, and particularly incising the cervico-vaginal tissue in a circular line. In the uterus manipulator according to the present invention, while the suturing procedure is performed by means of pushing the handle forward manually and moving the suture drive gear by rotating the handle after the suture control gear thereon is joined with the suture drive gear, the incising procedure, on the other hand, is performed by means of pulling the handle back manually, and after the incising control gear is joined with the incising drive gear, transferring the movement to the blade rotating gear, and the blade retainer, respectively, by rotating the handle. Thus, both the suturing procedure and the incising procedure can be performed by means of the manual push-pull movement, and there is no need for any external electrical energy.

Another important object of the present invention is to obtain a uterus manipulator that facilitates the procedure of incising and suturing of the uterus (womb), and related ligaments without harming other tissues and that prevents the incidence of various complications during said procedures. The uterus manipulator according to present invention ensures that the opening to be created after the incising of the cervico-vaginal region is determined before the incising, and said opening is fixed by circularly suturing with the desired number of stitches before the incising procedure, and subsequently, it ensures that the cervico-vaginal tissue is cut in a circular line. Thus, the suturing procedure is performed before the incising procedure, thereby eliminating complications and difficulties encountered during the incising and suturing procedure such as internal bleeding, accumulation of blood under the sutures (hematoma) or in the abdomen, internal scar tissue blood clots (for example, thrombosis, deep venous thrombosis or pulmonary embolism).

Yet another important object of the present invention is to ensure that both incising and suturing procedures are performed with a single manipulator that operates with minimal movement. In terms of its general elements, a manipulation process is performed in a single attempt, in which both functions (incising-suturing) are provided by the elements of head, suturing mechanism, incising mechanism, rotating ring, and handle.

The uterus manipulator according to the present invention offers a process that enables the movement of the uterus in both planes (horizontal and vertical), in which both functions are provided in a single attempt by means of the suturing mechanism and the incising mechanism thereof. Thus, the operation becomes less complicated and the operation time is shortened.

The uterine manipulator allows for performing the process of rotating the manipulator without causing any error. The rotating ring at the tip of the head is fixed to the organ where the manipulator is placed during the incising and suturing procedures, thereby ensuring that it does not slide back and forth and rotates easily on its own axis.

DESCRIPTION OF THE FIGURES

FIG. 2 illustrates the top isometric view of the head element included in the uterus manipulator.

FIG. 3 illustrates the bottom isometric view of the head element included in the uterus manipulator.

FIG. 6 illustrates the top isometric view of the suturing mechanism included in the uterus manipulator.

FIG. 7 illustrates the bottom isometric view of the suturing mechanism included in the uterus manipulator.

DESCRIPTION OF ELEMENTS/PARTS/COMPONENTS OF THE INVENTION

Figure 1:
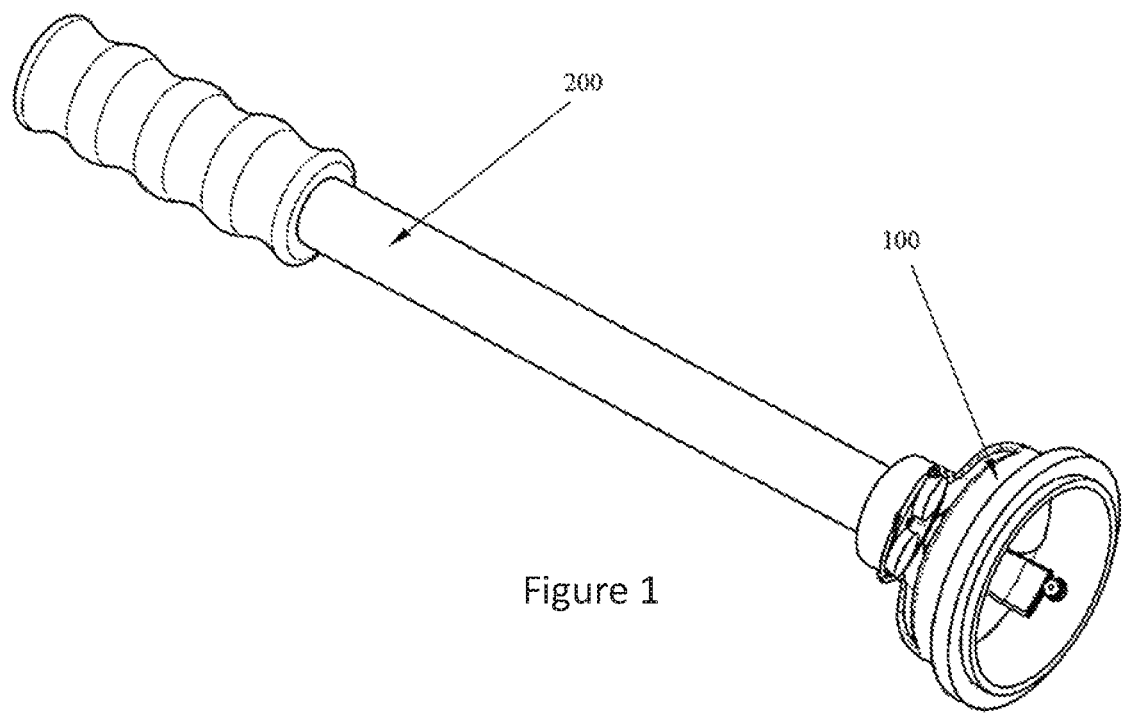
FIG. 1 illustrates the front isometric view of the uterus manipulator.
Figure 4:
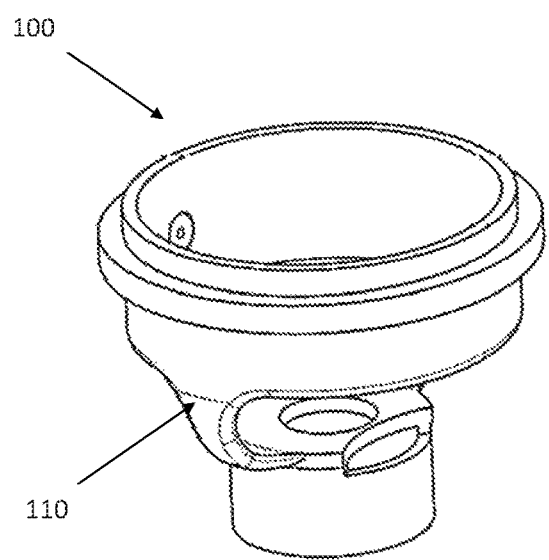
FIG. 4 illustrates the perspective view of the head element included in the uterus manipulator.
Figure 5:
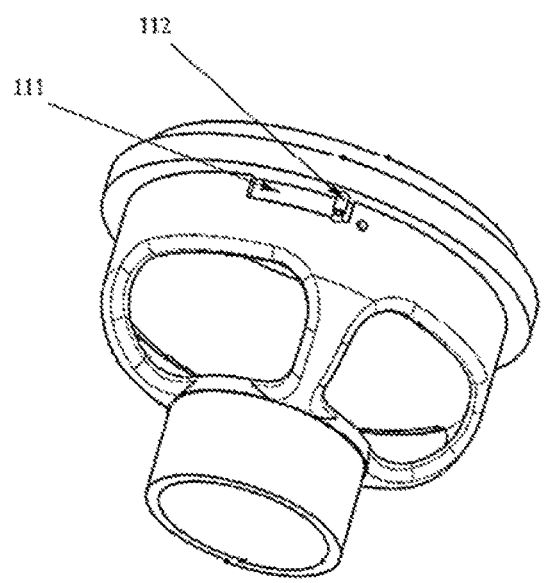
FIG. 5 illustrates another bottom isometric view of the head element included in the uterus manipulator.
Figure 8:
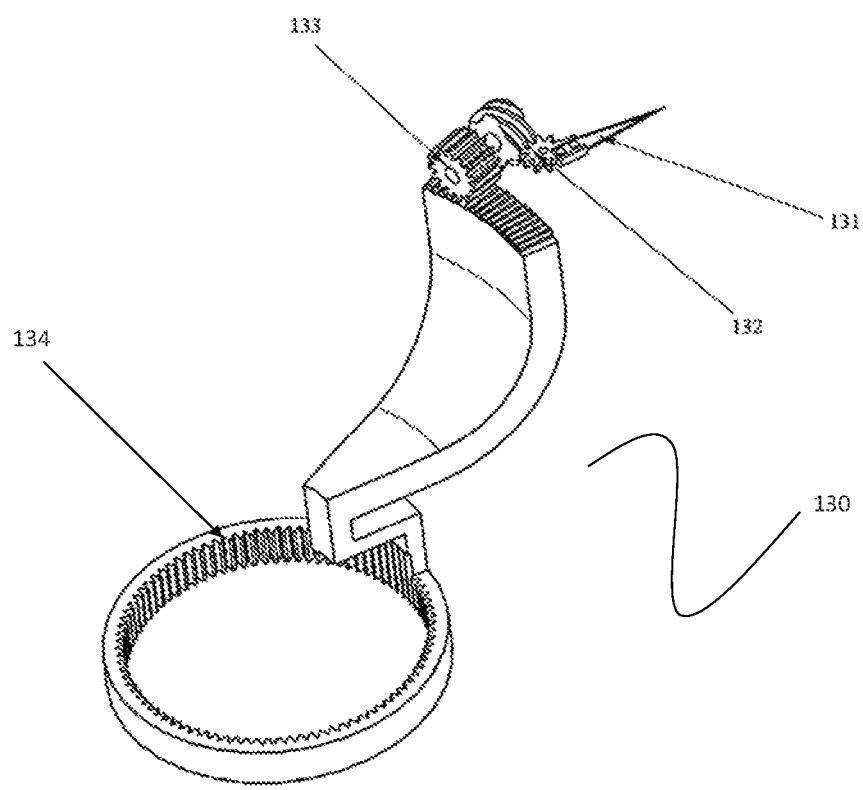
FIG. 8 illustrates the top isometric view of the incising mechanism included in the uterus manipulator.
Figure 9:
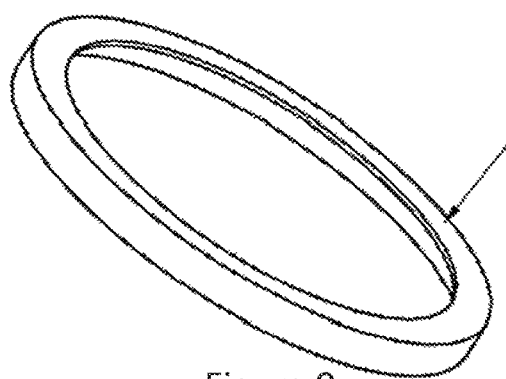
FIG. 9 illustrates the top isometric views of the rotating ring included in the uterus manipulator.
Figure 10:
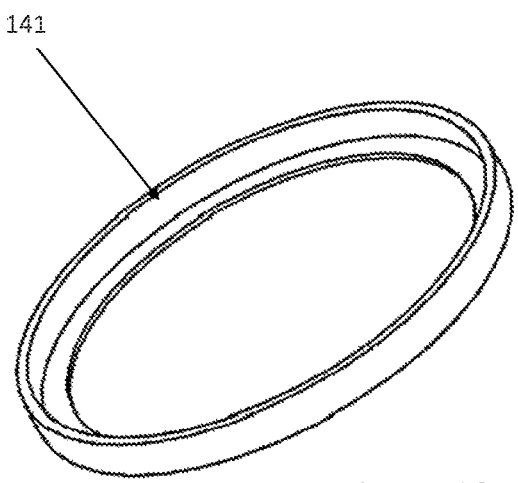
FIG. 10 illustrates the bottom isometric view of the rotating ring included in the uterus manipulator.
Figure 11:
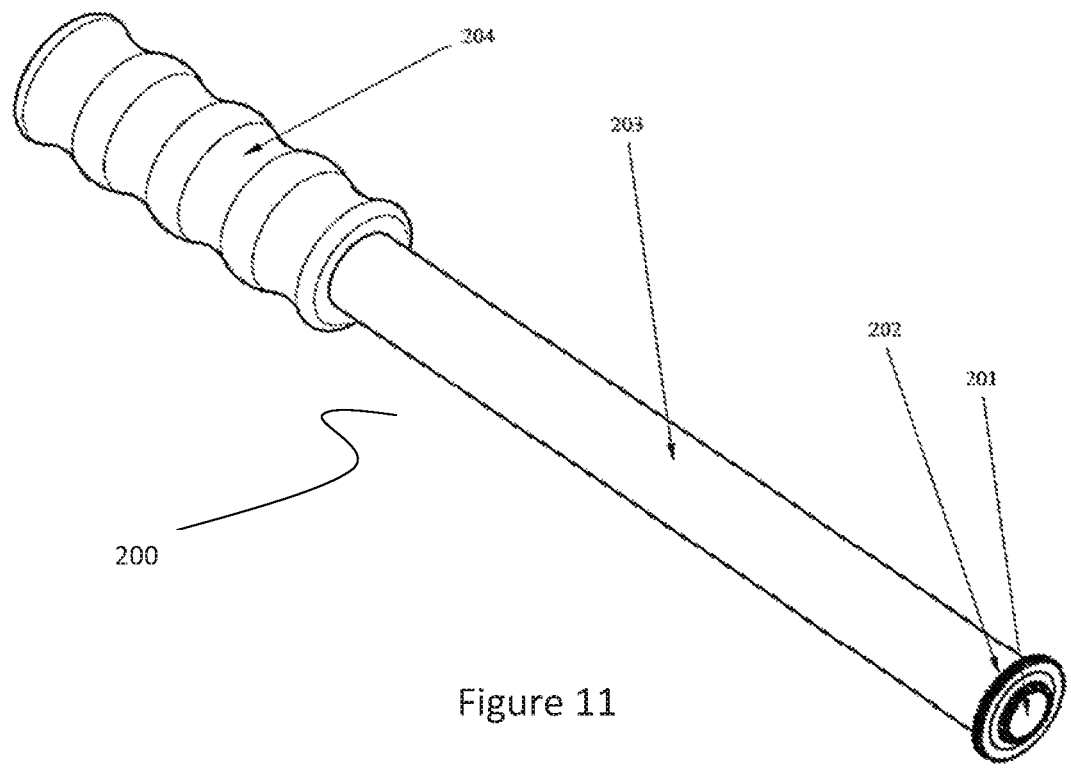
FIG. 11 illustrates the front isometric view of the handle element included in the uterus manipulator.
Figure 12:
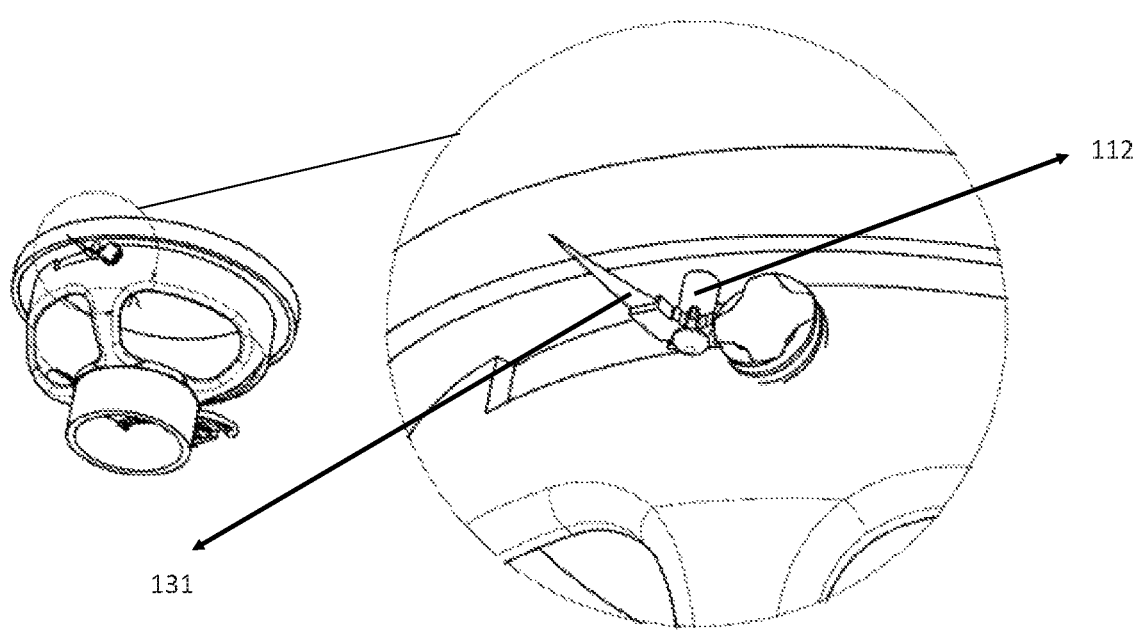
FIG. 12 illustrates the enlarged view of the blade shaft connecting the blade holder to the head body.

The parts and components in the figures are enumerated for a better explanation of the uterus manipulator developed with the present invention, and correspondence of every number is given below:

100. Head
110. Head Body
111. Blade Slot

112. Blade Rotating Shaft
113. Head Saddle
114. Head Tip
120. Suturing Mechanism
121. Needle
122. Needle Housing
123. Needle Rotating Drum
124. Suture Drive Gear
125. Suturing Mechanism Body
130. Incising Mechanism
131. Blade
132. Blade Retainer
133. Blade Rotating Gear
134. Incising Drive Gear
141. Rotating Ring
200. Handle
201. Suture Control Gear
202. Incising Control Gear
203. Shaft
204. Grip

DETAILED DESCRIPTION OF THE INVENTION

The present invention relates to a uterus manipulator in minimally invasive surgery that facilitates procedures of manipulation of the uterus, incising and suturing of all kinds of tissue connected to the uterus and particularly, incising the cervico-vaginal tissue in a circular line in laparoscopic hysterectomy, that prevents the incidence of various complications during said procedures, and that can be actuated (driven) manually without requiring any external energy source.

Uterus manipulator is a device that is used for uterus manipulation, incising and suturing of all kinds of tissue connected to the uterus and particularly, incising the cervico-vaginal tissue in a circular line, and in terms of its general elements, it comprises head (100), head body (110), suturing mechanism (120), incising mechanism (130), rotating ring (141), and handle (200).

Uterus manipulator comprises a head (100) including a ring-shaped rotating ring (141) that is positioned at head tip (114), and that prevents the manipulator from sliding back and forth on one hand, and that allows it to rotate easily around its own axis on the other hand, by means of being fixed to the organ in which it is placed during the incising and suturing procedures;

the suturing mechanism (120) that is positioned between the head body (110) and the head saddle (113), that allows for fixing/stitching the pre-determined cervico-vaginal opening before the incising procedure, including the needle (121) that has a spring shape and that enables fixing/stitching of the predetermined cervico-vaginal opening by circularly suturing with the desired number of stitches, the needle housing (122) that has a compatible shape with the spring shape of the needle (121) and groove into which the needle (121) can penetrate, and on which are two gapped region for actuating the needle (121) based on creating the friction force on its surface in order to perform the suturing process, at least two needle rotating drum (123) that contacts the needle (121) from the gapped regions of the needle housing (122) by means of the rotation of the gear wheel mounted thereon, thus, allowing the needle (121) to rotate in a circular orbit by means of creating a friction force thereon, the suture drive gear (124) that enables the rotation of at leas two gear wheels mounted on the needle rotation drum (123), the stitching mechanism body (125) in the form of a perforated plate that holds the needle housing (122), the needle rotating drum (123), and the stitch drive gear (124) together and that enables its stable positioning, and the incising mechanism (130) located in the head body (110), that allows for circularly incising the cervico-vaginal region, including the blade (131) forming the cervico-vaginal opening by circularly incising the cervico vaginal region, the blade retainer (132) that allows for transferring the necessary movement effect of the blade (131) to the blade (131) by means of the gear wheel system thereof, the blade rotating gear (133) that activates the gear wheel system of the blade retainer (132), the incising drive gear (134) that allows for transferring the movement to the blade rotating gear (133) by means of rotating the head body (110) via its teeth.

Said head (100) positions the blade slot (111) that enables the blade (131), which creates the cervico-vaginal opening by means of circularly incising the cervico-vaginal region, to move on a certain rectangular pattern while moving back and forth during the incising, and the blade shaft (112) that connects the blade retainer (132) to the head body (110) thereon.

The handle (200), which includes shaft (203) that is positioned between the distal and proximal ends of the head (100), and that has a cylindrical shape such that it is compatible with the vaginal anatomy of the patient, includes the disc-shaped suture control gear (201) that has drive teeth, which allows for activating the suture drive gears (124) in the suturing mechanism (120) when pushing forward at its proximal end to the head (100), and the disc-shaped incising control gear (202) that has a larger diameter value than the suture control gear, and that has drive teeth that allows for activating the incising drive gears (134) in the incising mechanism (130) when it is pulled back, grip (204) by which the pushing-forward, pulling-back, and the turning right-left movements are managed by means of holding manually at its distal end to the head (100).

The head body (110) is located under the rotating ring (141). The incising mechanism (130), on the other hand, is located on the head body (110), right under the rotating ring (141) at the head tip (114).

The uterus manipulation, the procedures of incising and suturing of all kinds of tissue connected to the uterus, and particularly, the procedure of incising the cervico-vaginal tissue in a circular line by the uterus manipulator are performed by means of the following operation method.

The operation method of the uterus manipulator of the present invention comprises the process steps of;
fixing the rotating ring (141) located at the head tip (113) to the cervico-vaginal region to be treated,
clamping/interacting the suture control gear (201) with the suture drive gears (124) by pushing the handle (200) by means of the grip (204),
actuating the suture drive gears (124) with the rotation of the suture control gear (201) by means of rotating the handle (200) after the clamping/interacting of the suture control gear and the suture drive gears (124),
rotating the needle rotating drum (123) by means of that the actuated suture drive gear (124) rotates the gear wheel mounted on the needle rotating drum (123),
Fixing/suturing the predetermined cervico-vaginal opening by the needle (121) by rotating in a circular orbit by means of that the rotating drum (123) that rotates creates a friction force on the needle (121) via contacting the needle (121) from the gapped regions of the needle housing (122), Following the suturing procedure, clamping/interacting the incising control gear (202) with the incising drive gear (134) by means of pulling back the handle (200) by the grip for the incising procedure, transferring the rotation movement to the blade rotating gear (133) and the blade retainer (132), respectively, by means of rotating the handle (200) after the incising control gear (200) clamps/interacts with the incising drive gear (134), creating the cervico-vaginal opening by circularly incising the cervico-vaginal region by the blade (131) via transferring the movement effect to the blade (131) by means of the gear wheel system of the blade retainer (132), and extracting the uterus through the vaginal route.

In the uterus manipulator, while the suturing procedure is performed by means of pushing the handle (200) forward manually via the grip (204) and moving the suture drive gear (124) by rotating the handle after the suture control gear (201) thereon is clamped/joined together with the suture drive gear (124), the incising procedure, on the other hand, is performed by means of pulling the handle (200) back manually via the grip (204), and after the incising control gear (202) is clamped/joined with the incising drive gear (134), transferring the movement to the blade rotating gear (133), and the blade retainer (132), respectively, by rotating the handle (200). Thus, both the suturing procedure and the incising procedure can be performed by means of the manual push-pull movement, and there is no need for any external electrical energy.

The uterus manipulator ensures that the opening to be created after the incising of the cervico-vaginal region is determined before the incising, and said opening is fixed by circularly suturing with the desired number of stitches before the incising procedure, and subsequently, it ensures that the cervico-vaginal tissue is cut in a circular line. Thus, the suturing procedure is performed before the incising procedure, thereby eliminating complications and difficulties encountered during the incising and suturing procedure such as internal bleeding, accumulation of blood under the sutures (hematoma) or in the abdomen, internal scar tissue blood clots (for example, thrombosis, deep venous thrombosis or pulmonary embolism).

The uterus manipulator offers a process that enables the movement of the uterus in both planes (horizontal and vertical), in which both functions (suturing-incising) are provided in a single attempt by means of the suturing mechanism and the incising mechanism thereof. Thus, the operation becomes less complicated and the operation time is shortened.

The rotating ring (141) at the head tip (114) is fixed to the organ where the manipulator is placed during the incising and suturing procedures, thereby ensuring that it does not slide back and forth and rotates easily on its own axis. It allows for performing the process of rotating the manipulator, which should be performed repeatedly during the incising and suturing procedures, without causing any error.

The invention claimed is:

1. A uterus manipulator that facilitates the procedures of manipulation of the uterus and incising and suturing cervico-vaginal tissue in a circular line in a laparoscopic hysterectomy, that prevents incidence of various complications during said procedures, and that can be driven manually without requiring any external energy source, characterized in that, the uterus manipulator comprises:

a head (100) defining a head body (110), a head saddle (113), and a head tip (114);

a suturing mechanism (120) that is positioned between the head body (110) and the head saddle (113), that allows for fixing/stitching a pre-determined cervico-vaginal opening before the incising procedure, the suturing mechanism (120) including:

a needle (121) that has a spring shape and that enables fixing/stitching of the predetermined cervico-vaginal opening by circularly suturing with a desired number of stitches;

a needle housing (122) that has a compatible shape with the spring shape of the needle (121) and a groove into which the needle (121) can penatrate, and on which are two gapped regions for actuating the needle (121) based on creating a friction force on a surface of the needle (121) in order to perform the suturing procedure;

at least two needle rotating drums (123) that contact the needle (121) from the gapped regions of the needle housing (122) by means of rotation of a gear wheel mounted on each of the at least two needle rotating drums (123), thus, allowing the needle (121) to rotate in a circular orbit by means of creating the friction force on the surface of the needle (121);

a suture drive gear (124) that enables the rotation of each gear wheel mounted on each of the at least two needle rotation drums (123); and a stitching mechanism body (125) in the form of a perforated plate that holds the needle housing (122), the at least two needle rotating drums (123), and the suture drive gear (124) together, and that enables stable positioning of the stitching mechanism body (125);

an incising mechanism (130) that is located in the head body (110), that allows for circularly incising a cervico-vaginal region, the incising mechanism (130) including:

a blade (131) configured to form a cervico-vaginal opening by circularly incising the cervico-vaginal region;

a blade retainer (132) that allows for transferring a necessary movement effect of the blade (131) to the blade (131) by means of a gear wheel system of the blade retainer (132);

a blade rotating gear (133) that activates the gear wheel system of the blade retainer (132); and an incising drive gear (134) that allows for transferring movement to the blade rotating gear (133) by means of rotating the head body (110) via teeth of the incising drive gear (134);

a ring-shaped rotating ring (141) that is positioned at the head tip (114), wherein the rotating ring (141) prevents the uterus manipulator from sliding back and forth and allows the uterus manipulator to rotate easily around an axis of the uterus manipulator, by means of being configured to fix to an organ in which it is placed during the incising and suturing procedures; and a handle (200) defining a proximal end and a distal end including:

a disc-shaped suture control gear (201) that has drive teeth, which allows for activating the suture drive gear (124) in the suturing mechanism (120) when pushing forward at the proximal end of the handle toward the head (100);

a disc-shaped incising control gear (202) that has a larger diameter value than the suture control gear, the incising control gear (202) comprising drive teeth that allow for activating the incising drive gear (134) in the incising mechanism (130) when pulled back;

a grip (204) by which the pushing-forward, the pulling-back, and a turning right-left movement are managed by means of manually holding the grip; and a shaft (203) that is positioned between a distal end of the grip and a proximal end of the head (100), wherein the shaft (203) has a diameter value compatible with the vaginal anatomy of a patient.

2. The uterus manipulator according to claim 1, characterized in that, the head (100) has a blade slot (111) that enables the blade (131), which creates the cervico-vaginal opening by means of circularly incising the cervico-vaginal region, to move in a rectangular pattern while moving back and forth during the incising.

3. The uterus manipulator according to claim 1, characterized in that, the head (100) includes a blade shaft (112), which connects the blade retainer (132) to the head body (110).

4. The uterus manipulator according to claim 1, characterized in that, the incising mechanism (130) is located on the head body (110), right under the rotating ring (141) at a proximal region of the head tip (114).

* * * * *